United States Patent
Roetzer

(12) 
(10) Patent No.: US 6,817,861 B1
(45) Date of Patent: Nov. 16, 2004

(54) DENTAL IMPRESSION DAM SYSTEM

(76) Inventor: Patrick L. Roetzer, 142 E. D St., Benicia, CA (US) 94510

( * ) Notice: Subject to any disclaimer, the term of this patent is extended or adjusted under 35 U.S.C. 154(b) by 0 days.

(21) Appl. No.: 10/120,292

(22) Filed: Apr. 9, 2002

(51) Int. Cl.⁷ .................................................. A61C 9/00
(52) U.S. Cl. .......................................... 433/37; 433/38
(58) Field of Search .............................. 433/37, 38, 39, 433/41, 42, 43, 44, 45, 46, 47, 48

(56) References Cited

U.S. PATENT DOCUMENTS

| | | | |
|---|---|---|---|
| 273,833 A | | 3/1883 | Fish |
| 310,404 A | | 1/1885 | Garner |
| 538,204 A | | 4/1895 | Traphagen |
| 3,534,475 A | | 10/1970 | Hilaire |
| 4,204,323 A | * | 5/1980 | Neubert et al. .............. 433/36 |
| 4,368,040 A | * | 1/1983 | Weissman ..................... 433/36 |
| 4,375,965 A | * | 3/1983 | Weissman ..................... 433/37 |
| 4,531,914 A | * | 7/1985 | Spinello ..................... 433/136 |
| 4,652,237 A | | 3/1987 | Cills |
| 5,102,335 A | * | 4/1992 | Getz .......................... 433/38 |
| 6,149,426 A | * | 11/2000 | Singer et al. ................ 433/37 |
| 6,379,147 B1 | * | 4/2002 | Georgakis et al. ............ 433/37 |

FOREIGN PATENT DOCUMENTS

EP          0 950 382 A2    10/1999

* cited by examiner

Primary Examiner—Ralph A. Lewis
(74) Attorney, Agent, or Firm—Theodore J. Bielen, Jr.

(57) ABSTRACT

A dental impression dam system utilizing an open tray forming a basin for dental impression material. The basin of the tray includes a gap at an extremity of the same. A flexible band of material bridges the gap of the tray basin and interacts with the dental material to form unit. The band adheres to the external wall portions of the tray when in place.

7 Claims, 2 Drawing Sheets

DENTAL IMPRESSION DAM SYSTEM

BACKGROUND OF THE INVENTION

The present invention relates to a novel and useful dental impression dam system.

Dental impression trays are employed generally to hold fluid impression material. The tray and material are inserted into a patient's mouth, and pressed onto the teeth of the patient to produce a pattern representing a dental formation. The fluid dental impression material then hardens and is used to produce a crown, bridge, and the like.

In most cases, the dental practitioner must introduce an adequate amount of material to produce a proper dental impression. However, in certain cases, excess material may be employed to insure against a deficiency of dental impression material during this process. However, the use of excess material creates a problem of the dental impression material overflowing the tray and gagging or choking the patient.

This problem has been recognized and various impression trays have been devised to correct the same. For example, U.S. Pat. Nos. 273,833, 4,652,237, and European Patent Application EPO 95038282 describe dental impression trays having dams at the end portions to prevent movement of impression material into the throats of the user.

U.S. Pat. Nos. 210,407 and 538,204 show dental impression trays which employ a soft dam material at the end portions thereof to hold the impression material in the tray and cushion the bite of the user on the impression material.

U.S. Pat. No. 3,534,475 shows an attachment for a dental impression tray in the form of a series of hooks which are meant to imbed excess dental impression tray material and hold the same away from the throat of the user.

A problem still remains in dental impression cup and trays in that the dams do not prevent the formation of a layer of excess dental impression material outside the tray which may separate from the prior art demand the main body of the impression material and cause a choking or gagging problem with the user or patient.

A dental impression dam system which solves the problems noted in the prior art would be a notable advance in the dental field.

BRIEF SUMMARY OF THE INVENTION

In accordance with the present invention a novel and useful dental impression tray system is herein provided.

The system of the present invention utilizes an open tray which forms a basin for dental impression material. Of course, the dental impression material, when introduced, would be fluid, hardening with time. The tray includes a bottom and a wall portion extending outwardly from the bottom leaving a gap in the wall portion at one of the extremities of the tray, usually the ID closest to the patient's throat when the dental impression tray is employed to make a dental bridge, crown, or the like.

A flexible band of material is employed to bridge the gap in the wall portion of the tray. The flexible band of material is selected to interact with the dental impression material to form a unit. Thus, the band of material must be porous to the dental impression material and be able to hold the same during and after hardening.

Means is also employed for adhering the flexible band of material to the open tray wall portions. Such adhering means may take the form of an adhesive which coats the porous flexible band of material without closing the pores of the same. Thus, the adhesive does not interfere with the penetration of the dental impression material with the band and the formation of a unit when the dental impression material hardens.

The dental impression tray of the present application may also be formed with openings to relieve the hydraulic pressure imposed by the dental impression material and to permit excess material to flow outwardly away from the end of the tray basin. In addition, soft tissue forming a portion of the dental impression is not distorted when hydraulic pressure is relieved through these openings.

It may be apparent that a novel and useful dental impression tray dam system has been hereinabove described.

It is therefore an object of the present invention to provide a dental impression tray dam system which utilizes flexible band to enclose the dental tray basin at its end portion and yet allow the patient to provide a dental impression without interference.

Another object of the present invention is to provide a dental impression tray dam system which utilizes a flexible band of porous material to enclose the basin of the dental tray in which interacts with the dental tray impression material to form a unit or unitary member, obviating excess dental impression tray material from entering the throat of the patient.

A further object of the present invention is to provide a dental impression tray dam system which is capable of capturing the impressions of edentulous and dentulous areas of the same arch of the patient.

A further object of the present invention is to provide a dental impression tray dam system which is usable with a variety of dental impression materials.

Another object of the present invention is to provide a dental impression tray which employs a dam system to direct the hydraulic pressure of the dental impression material toward the tissue and teeth resulting in improved detail of the dental impression.

Yet another object of the present invention is to provide a dental impression tray dam system which utilizes a band of soft porous material that can be hygienically or aseptically dispensed.

A further object of the present invention is to provide a dental impression tray dam system in which the movement of dental impression material down the throat of the patient is eliminated, while providing the practitioner with an excellent dental impression in both edentulous and dentulous areas of the same arch.

Another object of the present invention is to provide a dental impression tray which obtains a detailed dental impression, especially in the $2^{nd}$ and $3^{rd}$ molar areas.

Yet another object of the present invention is to provide a dental impression tray that eliminates an air bubble void at the $2^{nd}$ and $3^{rd}$ molar areas.

The invention possesses other objects and advantages especially as concerns particular characteristics and features thereof which will become apparent as the specification continues.

For a better understanding of the invention reference is made to the following detailed description of the preferred embodiments of the invention which should be referenced to the prior described drawings.

DETAILED DESCRIPTION OF THE PREFERRED EMBODIMENTS OF THE INVENTION

Various aspects of the present invention will evolve from the following detailed description of the preferred embodiments of the present invention which is best taken in conjunction with the prior delineated drawings.

Figure 1:
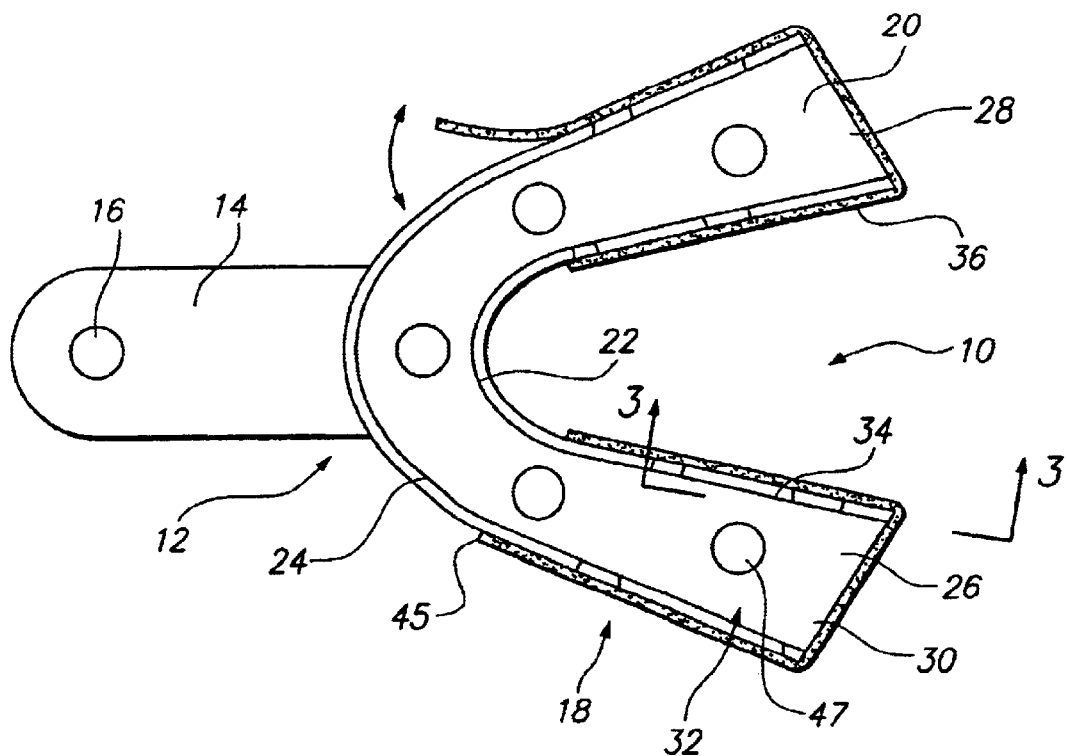
FIG. 1 is a top plan view of the system of the present invention as applied to a lower dental impression tray.

A preferred embodiment of the present invention is shown in its entirety in the drawings by reference character 10. System 10 possesses as one of its elements a tray member 12, which is a lower jaw tray. It should be noted that the dam system of the present invention also applies to an upper jaw dental impression tray having a single end. Tray member 12 includes a handle 14 with a placement opening 16 therethrough. A cup or container section 18 is also depicted in FIG. 1. Container 18 is formed with a bottom 20 and outwardly extending wall portions 22 and 24. Bottom 20 and wall portions 22 and 24 form a basin 26 to hold dental impression material, which will be discussed hereinafter. It should be noted that ends 28 and 30 of basin 26 are open, lacking any segment of wall portions 22 or 24. Plurality of openings 32 penetrate bottom 20 and wall portions 22 and 24 of container 18.

Open ends 28 and 30 of basin 26 are depicted in FIG. 1 as being enclosed by soft porous bands 34 and 36. As may be depicted in FIGS. 2 and 3 band 34 extends along wall portion 24 of tray container 18.

Figure 2:
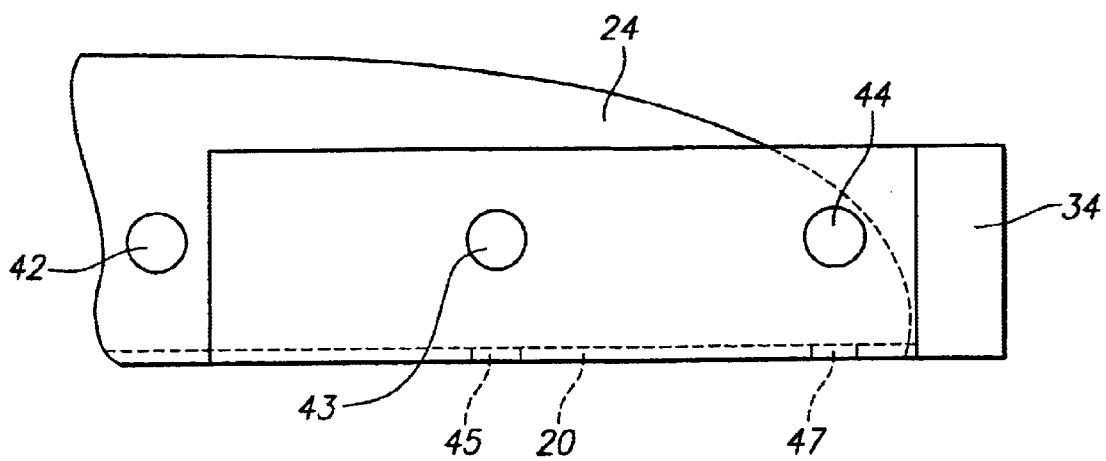
FIG. 2 is a partial side elevational view of a portion of the system depicted in FIG. 1.
Figure 3:
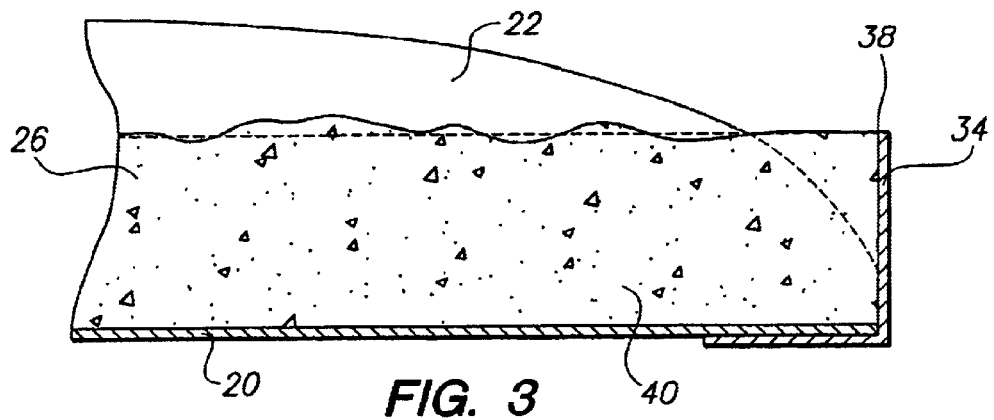
FIG. 3 is a sectional view of a portion of the tray depicted in FIG. 1 taken along line 3—3 thereof and further including the addition of dental impression material.

Bands 34 and 36 are held to wall portions 22 and 24 of container 18 by adhesive layers. For example, adhesive layer 38 with respect to band 34 is depicted in FIG. 3 to hold band 34 to wall portion 24 and bottom 20. Bands 34 and 36 may be hygienically dispensed using known techniques. Of course, a similar adhesive layer may be employed with respect to band 36. Most importantly, bands 34 and 36 are porous flexible elements which are compatible with dental impression material 40. That is to say, dental impression material 40 is capable of penetrating bands 34 and 36 to form a unit when material 40 hardens. It should be noted that adhesive layers, such as adhesive layer 38 does not effect the penetration of dental impression material 40 within bands 34 and 36. For example, bands 34 and 36 may be formed of a self adhering tape sold under the Trademark MICROPORE, distributed and manufactured by 3M Company of St. Paul, Minn. Likewise, the dental impression material may consist of vinyl polysiloxanes, irreversible colloids, such as alginate, reversible colloids, as well as any other modern dental impression material. It has been found that the dental impression material containing surfactants are particularly compatible with the system of the present invention. In addition, the light-bodied portion of a two-part dental impression material may be applied first to enhance penetration of bands 34 and 36 and insure binding of the heavier component thereafter. It should be noted that FIG. 2 shows openings 42, 43 and 44, of plurality of openings 32, through side 24 of container 18 and openings 45 and 47 through bottom 20, which tend to relieve the pressure of the dental impression material 40 found in basin 26. Bands 34 and 36 may extend over any of plurality of openings 32, such as openings 43 and 45, but are punctured for patency, allowing hydraulic pressure relief.

Figure 4:
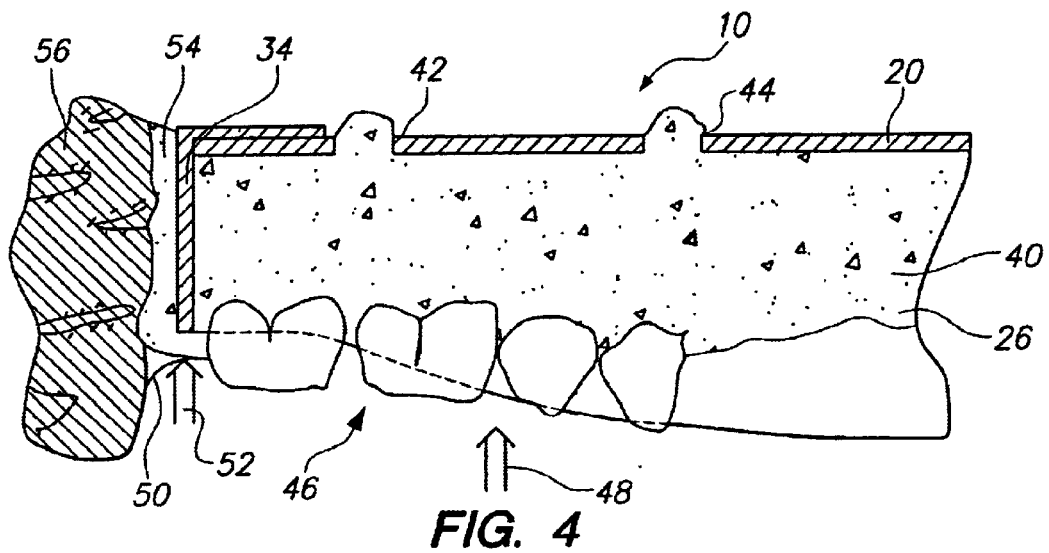
FIG. 4 is a sectional view similar to one depicted in FIG. 3 where the dental impression tray has been inverted and the teeth and tongue of a patient, have been added the latter depicted in section.
Figure 5:
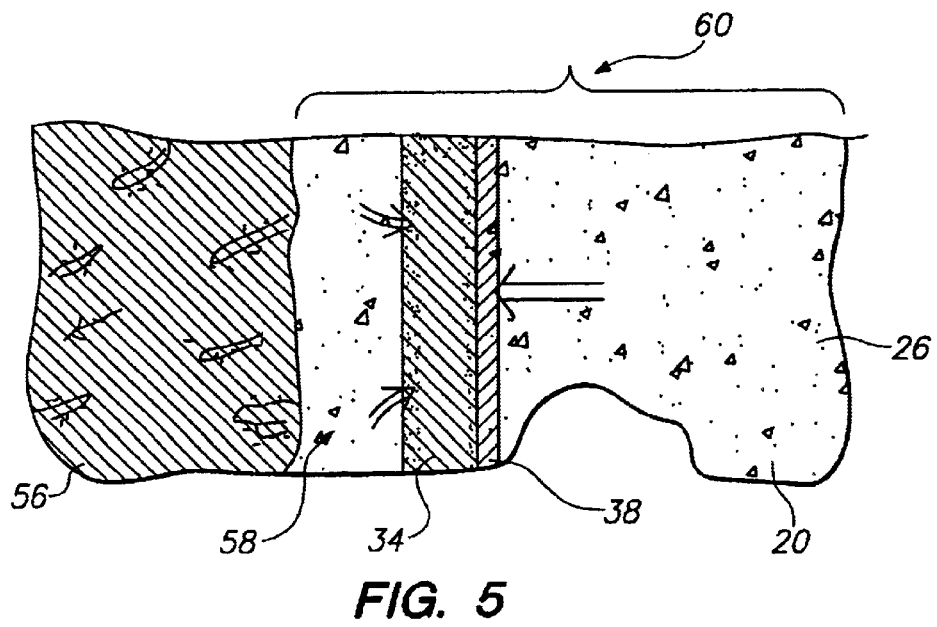
FIG. 5 is an enlarged sectional view indicating the formation of a unit between the porous band material and the dental impression material.

In operation, FIGS. 4 and 5 depict the obtaining of dental impression by a practitioner employing system 10 of the present invention on the lower jaw of a patient. The dental impression material 40 in tray 12, inverted from FIGS. 1–3, is pressed into the dentulous section 46 of the patient's lower jaw by the dental practitioner. Dental impression section 46 of a material 40 is still soft at this time, directional arrow 48. Portions of a gum 50 (edentulous area) may also be pressed into the dental impression material 40, directional arrow 52. As the practitioner wishes to obtain an accurate impression, a slight excess of dental impression material 40 may be employed within basin 26. Plurality of openings 32 through bottom 20 and walls 24 and 26 relieve hydraulic pressure and prevent the formation of air bubbles between the patient's dentulous and edentulous areas and the dental impression material 40. Also, a problem noted in the prior art is created in that a portion 54 of dental impression material may extend over flexible porous band 34 and lie adjacent the tongue 56, as well as the throat and palate (not shown) of the user. As the dental impression material 40 hardens, such portion 54 has, in the past, separated or calved causing gagging or choking of the patient. However, with reference to FIG. 5, it may be observed that dental impression material 20 has penetrated adhesive layer 38 and through band 34 from inside basin 26 and outside basin 26 adjacent tongue 56. Directional arrows 58, FIG. 5 indicate the penetration of dental impression material 40 throughout band 34. Upon hardening of dental impression material 40, a unit 60 is formed and is eventually moved when system 10 is taken from the mouth of the user. Gum area 50 also provides an edentulous impression since band 34 is flexible in the vertical direction as well. Thus, a superior dental impression is obtained using the system 10 of the present invention.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

What is claimed is:

1. A dental impression tray dam system using dental impression material for use in the mouth of a patient, comprising:

a. an open tray, said tray including a bottom and a wall portion extending outwardly therefrom, defining an open basin for the dental impression material, said open basin including an end portion intended to lie distally from the entrance to the mouth of the patient, said outwardly extending wall portion of said open basin forming at least one gap thereof at said end portion of said open basin;

b. a flexible band of material bridging said at least one gap in said outwardly extending wall portion of said end of said open basin, said flexible band of material interacting with dental impression material positioned in said basin to form a unit; and c. means for adhering said flexible band of material to said open tray.

2. The system of claim 1 in which said tray comprises an angulated member forming an angulated basin.

3. The system of claim 2 which further comprises at least one opening through said wall portion of said tray.

4. The system of claim 2 in which said band of flexible material comprises a porous material.

5. The system of claim 4 in which said means for adhering said flexible band of material to said open tray comprises an adhesive coated to said porous flexible material and maintaining said porosity.

6. The system of claim 5 in which said tray comprises an angulated member forming an angulated basin.

7. The system of claim 6 which further comprises at least one opening through said wall portion of said tray.

* * * * *